(12) United States Patent
Rowe

(10) Patent No.: US 8,460,366 B2
(45) Date of Patent: Jun. 11, 2013

(54) TRANSCATHETER HEART VALVE WITH MICRO-ANCHORS

(75) Inventor: Stanton Rowe, Newport Beach, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 121 days.

(21) Appl. No.: 13/185,254

(22) Filed: Jul. 18, 2011

(65) Prior Publication Data
US 2012/0016470 A1  Jan. 19, 2012

Related U.S. Application Data

(63) Continuation of application No. 12/252,161, filed on Oct. 15, 2008, now Pat. No. 7,981,151.

(60) Provisional application No. 60/980,112, filed on Oct. 15, 2007.

(51) Int. Cl.
*A61F 2/82* (2006.01)

(52) U.S. Cl.
USPC ....... 623/1.36; 623/1.11; 623/1.24; 623/1.27; 623/1.15

(58) Field of Classification Search
CPC ..................................... A61F 2/82; A61F 2/95
USPC ....... 623/1.36, 2.1–2.19, 1.24–1.27, 1.1–1.23
See application file for complete search history.

(56) References Cited

U.S. PATENT DOCUMENTS

| 5,053,047 | A | 10/1991 | Yoon |
| 5,254,127 | A | 10/1993 | Wholey et al. |
| 5,500,000 | A | 3/1996 | Feagin et al. |
| 5,569,272 | A | 10/1996 | Reed et al. |
| 5,695,469 | A | 12/1997 | Segal |
| 5,814,051 | A | 9/1998 | Wenstrom, Jr. |
| 5,980,530 | A | 11/1999 | Willard et al. |
| 6,231,561 | B1 | 5/2001 | Frazier et al. |

(Continued)

FOREIGN PATENT DOCUMENTS

| WO | 2004103223 | 12/2004 |
| WO | 2006127756 | 11/2006 |
| WO | 2007053243 | 5/2007 |

OTHER PUBLICATIONS

International Search Report for PCT/US2008/090004, Dated: Jan. 14, 2009.

*Primary Examiner* — Jason-Dennis Stewart
(74) *Attorney, Agent, or Firm* — David L. Hauser

(57) ABSTRACT

Various embodiments of methods and apparatus for treating defective heart valve are disclosed herein. In one exemplary embodiment, a transcatheter heart valve is disclosed that includes an expandable shape memory stent and a valve member supported by the stent. A plurality of micro-anchors can be disposed along an outer surface of the stent for engaging native tissue. The transcatheter heart valve can be configured to be advanced into a dilated valve annulus via a balloon catheter. The balloon can be inflated to expand the transcatheter heart valve from a collapsed diameter to an over-expanded diameter such that the micro-anchors engage tissue along the surrounding valve annulus. After engaging the tissue, the balloon can be deflated and the shape memory stent can retract or recoil toward its predetermined recoil diameter. As the stent recoils, the surrounding tissue is pulled inward by the stent such that the diameter of the valve annulus is reduced.

14 Claims, 7 Drawing Sheets

U.S. PATENT DOCUMENTS

| | | |
|---|---|---|
| 6,334,873 B1 | 1/2002 | Lane et al. |
| 6,530,952 B2 | 3/2003 | Vesely |
| 6,599,310 B2 | 7/2003 | Leung et al. |
| 6,695,878 B2 | 2/2004 | McGuckin, Jr. et al. |
| 6,730,118 B2 | 5/2004 | Spenser et al. |
| 6,767,362 B2 | 7/2004 | Schreck |
| 6,893,460 B2 | 5/2005 | Spenser et al. |
| 6,932,838 B2 | 8/2005 | Schwartz et al. |
| 6,991,643 B2 | 1/2006 | Saadat |
| 7,041,128 B2 | 5/2006 | McGuckin, Jr. et al. |
| 7,144,415 B2 | 12/2006 | Del Rio et al. |
| 7,160,312 B2 | 1/2007 | Saadat |
| 7,351,258 B2 | 4/2008 | Ricotta |
| 2002/0052640 A1* | 5/2002 | Bigus et al. ............... 623/1.11 |
| 2003/0114913 A1 | 6/2003 | Spenser et al. |
| 2004/0024362 A1 | 2/2004 | Trout, III |
| 2005/0033367 A1 | 2/2005 | Leung et al. |
| 2005/0102024 A1 | 5/2005 | Riccotta et al. |
| 2005/0137691 A1 | 6/2005 | Salahieh et al. |
| 2006/0004442 A1 | 1/2006 | Spenser et al. |
| 2006/0127756 A1 | 6/2006 | Seo |
| 2006/0190074 A1 | 8/2006 | Hill et al. |
| 2006/0217794 A1 | 9/2006 | Ruiz et al. |
| 2006/0256136 A1 | 11/2006 | O'Donnell et al. |
| 2007/0005109 A1 | 1/2007 | Popadiuk et al. |
| 2007/0005129 A1 | 1/2007 | Damm et al. |
| 2007/0005131 A1 | 1/2007 | Taylor |
| 2007/0066993 A1 | 3/2007 | Kreidler |
| 2007/0088431 A1 | 4/2007 | Bourang et al. |
| 2007/0093890 A1 | 4/2007 | Eliasen et al. |
| 2007/0100440 A1* | 5/2007 | Figulla et al. ............... 623/2.18 |
| 2007/0112425 A1 | 5/2007 | Schaller et al. |
| 2007/0282429 A1 | 12/2007 | Hauser et al. |
| 2007/0293942 A1 | 12/2007 | Mirzaee |
| 2008/0208327 A1 | 8/2008 | Rowe |

\* cited by examiner

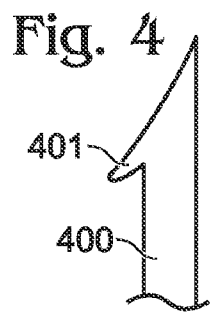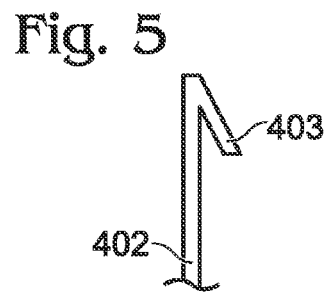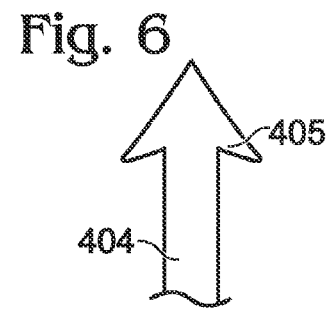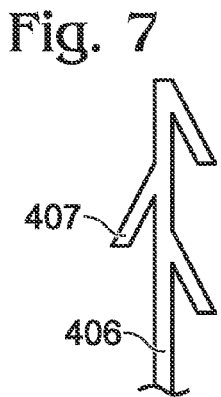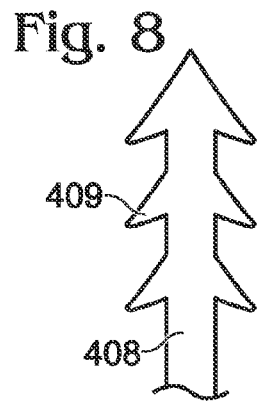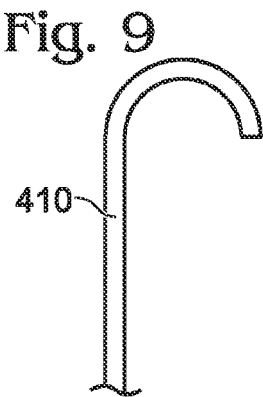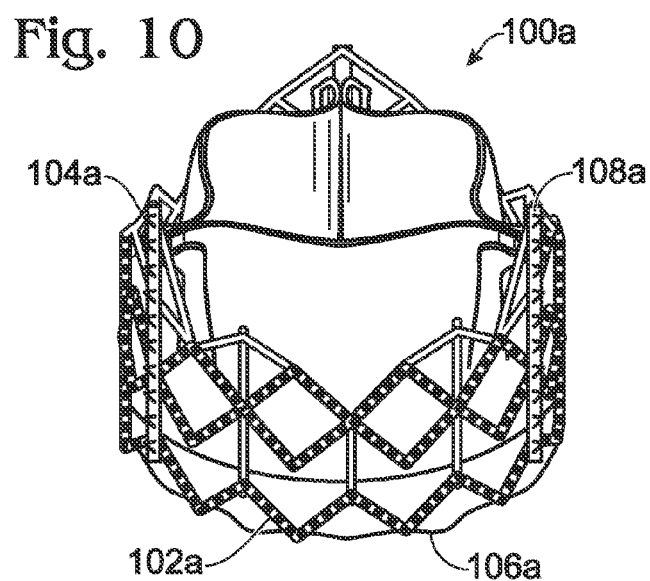

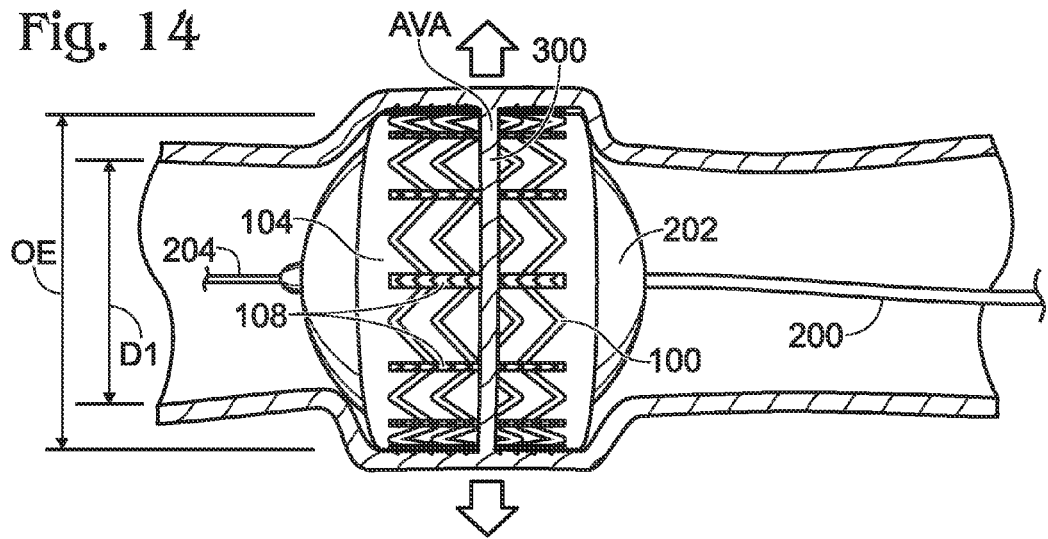
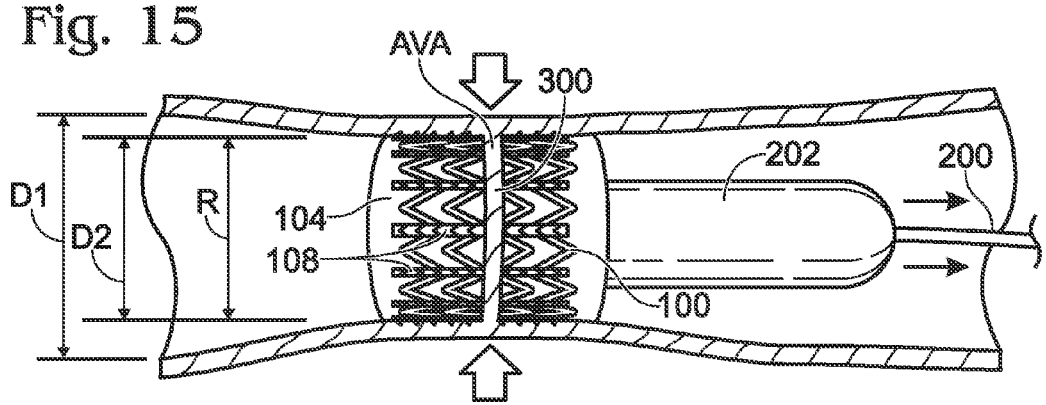
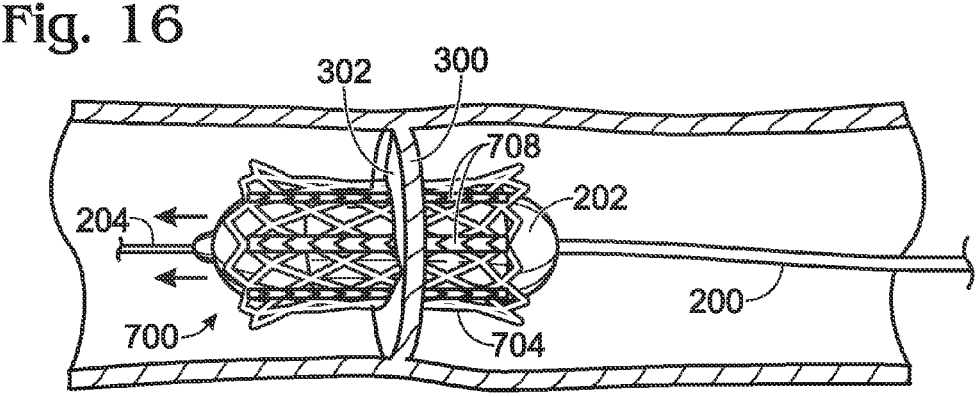

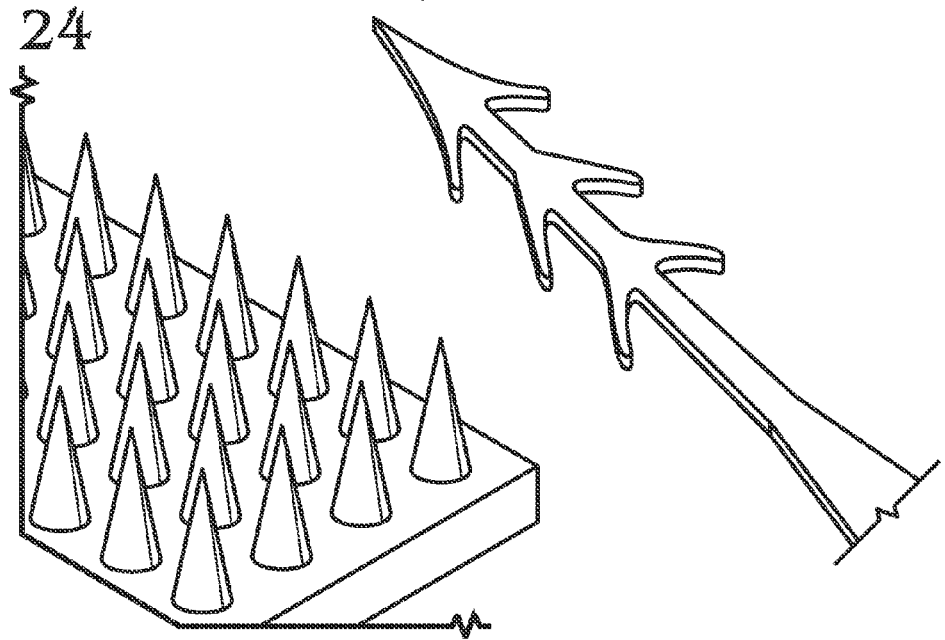
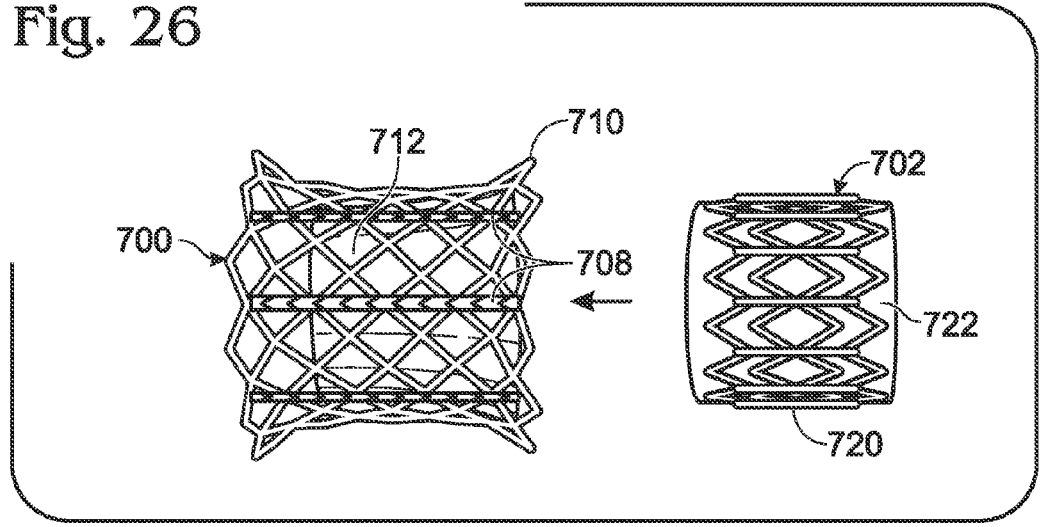

TRANSCATHETER HEART VALVE WITH MICRO-ANCHORS

CROSS-REFERENCE TO RELATED APPLICATIONS

The present application is a continuation of U.S. application Ser. No. 12/252,161, filed Oct. 15, 2008, which claims the benefit of U.S. Provisional Application No. 60/980,112, filed Oct. 15, 2007, which is incorporated herein by reference.

FIELD

The disclosed technology relates generally to methods and devices for improving valve function of a heart. For instance, embodiments of the disclosed technology can be used to treat aortic insufficiency in a human heart.

BACKGROUND

The aortic valve in the human heart is a one-way valve that separates the left ventricle from the aorta. The aorta is a large artery that carries oxygen-rich blood out of the left ventricle to the rest of the body. Aortic insufficiency is a condition in which the aortic valve does not fully close during ventricular diastole, thereby allowing blood to flow backward from the aorta into the left ventricle. This leakage of blood through the aortic valve back into the left ventricle is often referred to as aortic valve regurgitation.

Aortic insufficiency is typically caused by aortic root dilatation (annuloaortic ectasia), which is idiopathic in over 80% of the cases. Aortic insufficiency may also result from other factors, such as aging and hypertension. In any case, the regurgitation of blood resulting from aortic insufficiency substantially reduces the pumping efficiency of the left ventricle. Therefore, even during periods of rest, the heart must work hard simply to maintain adequate circulation through the body. Over time, this continuous strain on the heart can damage the left ventricle. For example, the additional strain on the heart may result in a thickening of the heart muscle (hypertrophy). When heart-wall thickening occurs due to aortic insufficiency, the geometry of the heart can be adversely affected and the heart can be permanently damaged.

Although aortic insufficiency is relatively common, the treatment of this condition still represents a substantial clinical challenge for surgeons and cardiologists. For example, because aortic insufficiency has a long latency period, afflicted patients may already be at significant risk for heart failure by the time the symptoms arise. In many cases, when patients are not monitored well for aortic insufficiency and are left untreated, the patient's left ventricle may become irreversibly damaged before therapy can be delivered. Therefore, even if a defective aortic valve is replaced with a prosthetic valve, the patient may never fully recover and their survival rate may be substantially impaired.

Existing methods of treating aortic insufficiency suffer from a number of significant disadvantages. For example, open heart surgical valve replacement is often too traumatic for older and/or frail individuals. Replacement of the aortic valve using existing catheterization techniques is also challenging because it is difficult to anchor a prosthetic valve within a soft and dilated annulus. More particularly, when a prosthetic valve is delivered to the site of the aortic valve and expanded, it engages and continuously exerts an outward force against the aortic valve wall. This continuous outward pressure is necessary for anchoring the prosthetic valve within the native valve but may also cause the already-dilated native aortic annulus to become further expanded. The tissue along the annulus of a valve suffering from aortic insufficiency is typically soft and flexible (as opposed to being hard and calcified as with aortic stenosis) and therefore the further expansion of the aortic annulus may lead to dislodgement of the prosthetic valve. Such dislodgement could require delivery of a still larger valve or result in death of the patient. A prosthetic valve with a very large diameter may be delivered via a catheterization technique to reduce the possibility of dislodgement. However, it follows that such a valve would also have a large diameter in its crimped condition. The delivery of such a large-diameter prosthetic valve is much more challenging and dangerous than the delivery of a relatively small prosthetic valve of the type currently used to treat aortic stenosis.

Therefore, a need exists for new and improved methods and devices for treating aortic insufficiency.

SUMMARY

Embodiments of the disclosed technology are directed to percutaneous (e.g., catheter-based) and/or minimally invasive surgical (MIS) procedures for treating aortic insufficiency. These less invasive therapies, which do not require open-heart surgery, provide patients with a more attractive option for early treatment of aortic insufficiency, thus mitigating or even avoiding the risk of damage to the left ventricle. These less invasive therapies also provide an urgently needed treatment option for patients who cannot be treated by open-heart surgery because they are too sick or frail to withstand the treatment. Unfortunately, at the present time, these "high-risk" patients are typically left untreated.

According to one exemplary embodiment disclosed herein, a system is provided for replacing the native aortic valve using a catheter-based approach. The system includes a transcatheter heart valve (THV), sometimes referred to herein as a "bioprosthesis." The transcatheter heart valve of this embodiment comprises a support structure, such as a stent, formed of, for example, a shape-memory material. The support structure can be configured to be radially compressible into a compressed state, expandable into an over-expanded state having a first diameter, and self-adjustable into a functional state having a second diameter less than the first diameter. The transcatheter heart valve can also include a flexible valve member or membrane, such as a prosthetic one-way valve member, within an interior of the support structure. In particular implementations, one or more grabbing mechanisms such as micro-anchors, are disposed on an outer surface of the support structure, where the grabbing mechanisms can be configured to penetrate or otherwise securably engage the support structure to surrounding native tissue, such as along a valve orifice when the support structure is expanded within the valve orifice.

In particular implementations, at least one of the one or more grabbing mechanisms comprises a projection having a hook, a sharpened barb, tree-shaped barbs, or an anchor-shaped barb. In some embodiments, at least one of the one or more grabbing mechanisms comprises a strip of projections disposed circumferentially around the support structure. In other implementations, at least one of the one or more grabbing mechanisms comprises a strip of projections disposed along a vertical axis of the support structure. At least one of the one or more grabbing mechanisms can include a projection that changes shape after a period of time. For example, the projection can be initially held in an undeployed state by a resorbable material.

The support structure, the one or more grabbing mechanisms, or both the support structure and the one or more grabbing mechanisms can be formed of a shape memory alloy, such as of Nickel-Titanium (Nitinol), in some embodiments. The support structure can be constructed with sufficient radial strength to maintain the native aortic valve in a dilated condition such that the prosthetic valve member can effectively replace the function of the native aortic valve, but is configured such that its diameter is not substantially greater than the native valve's diameter.

The flexible membrane can be a valve assembly having an inlet side and an outlet side, the valve assembly being configured to allow flow from the inlet side to the outlet side but prevent flow from the outlet side to the inlet side. In some embodiments, the flexible membrane is configured to replace an aortic valve.

Embodiments of a prosthetic heart valve can comprise an inner and outer support structure that can be delivered separately from one another. For example, one embodiment comprises an outer support structure configured to be radially compressible, expandable into an over-expanded state having a first diameter, and self-adjustable into a functional state having a second diameter less than the first diameter. The prosthetic heart valve can also comprise one or more grabbing mechanisms disposed on an outer surface of the outer support structure, the one or more grabbing mechanisms being configured to penetrate or otherwise securably engage the outer support structure to surrounding native tissue, and an inner support structure configured to be radially compressible and expandable into an expanded state within the interior of the outer support structure, where a flexible valve member can be secured within an interior of the inner support structure.

As with other embodiments, embodiments comprising an inner and outer support structure can also include at least one grabbing mechanism that comprises a projection having a hook, a sharpened barb, tree-shaped barbs, or an anchor-shaped barb. One or more of the outer support structure, the inner support structure, or the one or more grabbing mechanisms can be formed of a shape memory alloy. The flexible membrane can be configured to replace an aortic valve. The inner support structure can be configured to securably engage the interior of the outer support structure upon being expanded within the outer support structure.

In one exemplary method disclosed herein, the transcatheter heart valve can be "over-expanded" within a native aortic valve using a balloon catheter. More particularly, an expandable prosthetic heart valve can be positioned within a patient's aortic valve and expanded, such as by inflating a balloon of a balloon catheter around which the prosthetic heart valve is disposed, to an over-expanded diameter thereby causing one or more projections on an outer surface of the prosthetic heart valve to engage native tissue of the patient's aortic valve. The prosthetic heart valve can be allowed to retract toward a recoil diameter less than the over-expanded diameter (e.g., a "memorized" (if the support structure comprises a shape-memory alloy) or "recoil" diameter), such as by deflating the balloon. As the prosthetic heart valve recoils (reduces in diameter), the one or more projections are engaged with the native tissue of the patient's aortic valve, thereby reducing a diameter of the patient's native aortic valve. This can occur because the projections (e.g. micro-anchors) on the support structure are securely engaged with the tissue of the valve annulus. Conventional valves cannot undergo such over-expansion due to materials used and methods of manufacture.

In some embodiments, the expandable prosthetic heart valve comprises a support structure made of a shape memory alloy that causes the support structure to have the recoil diameter when the support structure is not acted on by any external force. In certain embodiments, the one or more projections include hooks, barbs, or anchors. At least one of the one or more projections changes its shape after penetrating the native tissue of the patient's aortic valve in some embodiments.

This exemplary method of implanting an over-expanded transcatheter heart valve has a number of advantageous features over known transcatheter heart valves. For example, unlike existing transcatheter heart valves, the over-expanded transcatheter heart valve does not apply an outward radial force on the native valve annulus after implantation. This is advantageous because, as discussed above, a regurgitating valve typically results from a diseased or aging valve annulus that is already substantially dilated. The application of a continuous outward radial force on a weakened and dilated annulus will usually dilate the annulus further. This could result in serious damage to the anatomical structure of the heart and, as the weakened aortic root dilates further, could eventually lead to dislodgement of the transcatheter heart valve.

By reducing the diameter of the surrounding annulus, it is also possible to replace the native aortic valve using a smaller transcatheter heart valve than would be typically required to treat aortic insufficiency. Due to the recoil of the support structure, the final diameter of the over-expanded transcatheter heart valve is substantially smaller than a conventional THV. A conventional THV must be expanded to a diameter that is capable of being securely maintained in a dilated valve annulus, whereas the over-expanded transcatheter heart valve constricts the annulus and therefore can have a smaller outer diameter. As a result of the smaller final diameter, the over-expanded transcatheter heart valve can also employ a smaller valve member. The smaller valve member allows the over-expanded transcatheter heart valve to be crimped to a much smaller diameter and have a smaller profile during advancement through the patient's vasculature. It will be recognized by those skilled in the art that a smaller diameter facilitates advancement of the transcatheter heart valve through a patient's vasculature.

Some methods for treating aortic insufficiency can comprise a two-stage delivery. For example, one method comprises positioning an outer stent within a patient's aortic valve, expanding the outer stent to an over-expanded diameter, thereby causing projections on the outer surface of the outer stent to engage tissue of the patient's aortic valve, allowing the outer stent to retract toward a recoil diameter that is less than the over-expanded diameter while the projections are engaged with the tissue of the patient's aortic valve, thereby causing the diameter of the patient's native aortic valve to be reduced, positioning a prosthetic heart valve within the outer stent, and expanding the prosthetic heart valve while the prosthetic heart valve is positioned within the outer stent.

In some embodiments, the act of expanding the prosthetic heart valve comprises frictionally securing the prosthetic heart valve within the outer stent, engaging grooves provided within the outer stent with complementary members of the prosthetic heart valve, or engaging a snap mechanism that causes the prosthetic heart valve to be secured within the outer stent, and/or inflating a balloon of a balloon catheter around which the outer stent is disposed. In certain embodiments, the act of allowing the outer stent to retract comprises deflating the balloon of the balloon catheter. In some methods, the outer stent comprises a shape memory alloy. In some methods, the prosthetic heart valve comprises a compressible and expandable inner support structure and a valve membrane secured in an interior of the inner support structure The foregoing and other features and advantages of the invention will become more apparent from the following detailed description, which proceeds with reference to the accompanying figures.

BRIEF DESCRIPTION OF THE DRAWINGS

FIG. 4 shows an elevation view of one embodiment of a projection (or micro-anchor) that can be used with embodiments of a transcatheter heart valve.

FIG. 5 illustrates an elevation view of another embodiment of a projection (or micro-anchor) that can be used with a transcatheter heart valve.

FIG. 6 illustrates an elevation view of another embodiment of a projection (or micro-anchor) that can be used with a transcatheter heart valve.

FIG. 7 illustrates an elevation view of another embodiment of a projection (or micro-anchor) that can be used with a transcatheter heart valve.

FIG. 8 illustrates an elevation view of another embodiment of a projection (or micro-anchor) that can be used with a transcatheter heart valve.

FIG. 9 illustrates an elevation view of another embodiment of a projection (or micro-anchor) that can be used with a transcatheter heart valve.

FIG. 10 is a perspective view of a transcatheter heart valve formed with a shape memory support structure in accordance with another embodiment of the disclosed technology.

FIGS. 12-15 are simplified sectional views of a transcatheter heart valve being deployed in accordance with an embodiment of the disclosed technology.

FIGS. 16-20 show simplified sectional views of one embodiment of a transcatheter heart valve being deployed in a two-stage process according to an exemplary method of the disclosed technology.

FIGS. 21-25 show perspective views of additional embodiments of projections (or micro-anchors) that can be used with a transcatheter heart valve.

FIG. 26 is an elevation view of another embodiment of a transcatheter heart valve according to the disclosed technology. In particular, the embodiment illustrated in FIG. 26 has two attachable sections.

DETAILED DESCRIPTION

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

Figure 1:
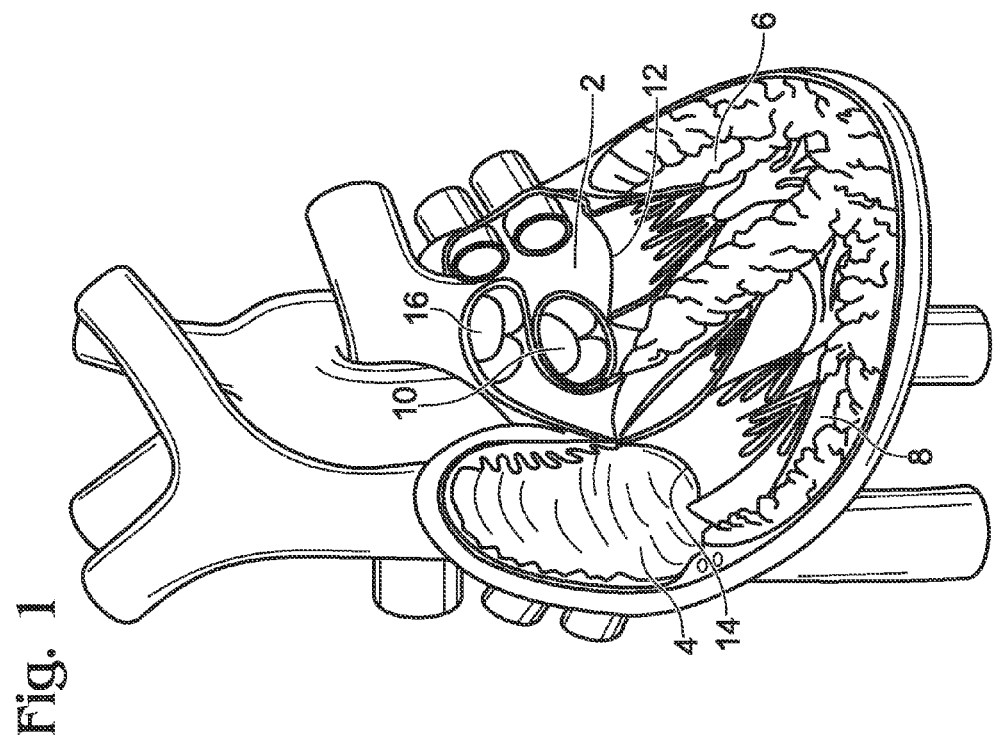
FIG. 1 is an anatomic anterior view of a human heart, with portions broken away and in section to view the interior heart chambers and adjacent structures.

In vertebrate animals, the heart is a hollow muscular organ having four pumping chambers as seen in FIG. 1. The left and right atria 2, 4 and the left and right ventricles 6, 8, are each provided with their own one-way valve. The natural heart valves are identified as the aortic 10, mitral (or bicuspid) 12, tricuspid 14, and pulmonary 16, and are each mounted in an annulus comprising dense fibrous rings attached either directly or indirectly to the atrial and ventricular muscle fibers. Each annulus defines a flow orifice.

The atria 2, 4 are the blood-receiving chambers, which pump blood into the ventricles 6, 8. The ventricles 6, 8 are the blood-discharging chambers. The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves 10, 12, 14, 16 ensure that blood does not flow in the wrong direction during the cardiac cycle; that is, to ensure that the blood does not back flow from the ventricles 6, 8 into the corresponding atria 2, 4, or back flow from the arteries into the corresponding ventricles 6, 8. The mitral valve 12 is between the left atrium 2 and the left ventricle 6, the tricuspid valve 14 between the right atrium 4 and the right ventricle 8, the pulmonary valve 16 is at the opening of the pulmonary artery, and the aortic valve 10 is at the opening of the aorta. As discussed, in aortic insufficiency, the aortic valve 10 can become dilated, thus preventing the valve from fully closing. Embodiments of the present disclosure can be deployed to the aortic valve, specifically to the area of the aortic valve annulus, to treat aortic insufficiency.

Figures 2, 3:
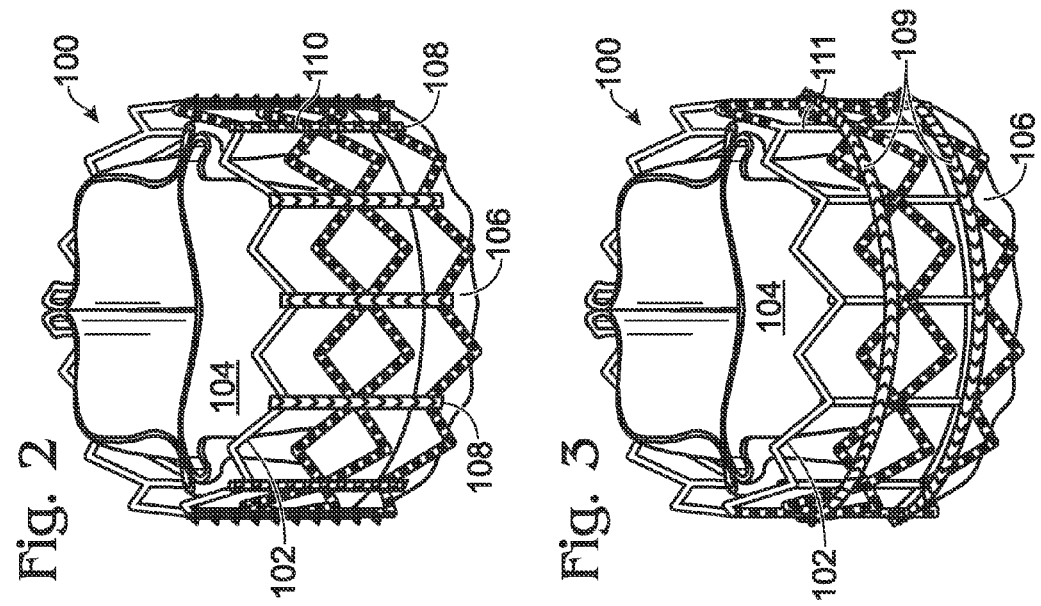
FIG. 2 is a perspective view of a transcatheter heart valve formed with a shape-memory stent in accordance with an embodiment of the disclosed technology.
FIG. 3 is a perspective view of another embodiment of a transcatheter heart valve formed with a shape memory support structure according to the disclosed technology.

FIG. 2 is a perspective view of an exemplary transcatheter heart valve 100 (also referred to as bioprosthesis 100). Bioprosthesis 100 includes a tubular support structure 102, a flexible membrane 104 (e.g., a valve member), a membrane support 106, and one or more grabbing mechanisms 108 affixed about a circumference of the support structure 102.

The support structure 102 in FIG. 2 can be formed of a shape memory material, such as Nitinol. In one exemplary embodiment, the support structure 102 can be radially compressed into a compressed state for delivery through the patient's vasculature, but can self expand to a natural, uncompressed or functional state having a preset diameter. In other words, the support structure 102 moves or tends toward a preset diameter when free of external forces. Furthermore, the support structure 102 can be expanded beyond its natural diameter to an over-expanded diameter. After the support structure 102 is in this over-expanded state, the support structure returns toward its preset diameter (or naturally recoils to the preset or recoil diameter).

The support structure 102 can be generally tubular in shape and has a longitudinal flow path along its structural axis. The support structure 102 can include a grated framework, such as a stent, configured to secure bioprosthesis 100 within or adjacent to the defective valve annulus of the heart. The support structure 102 further provides stability and prevents the bioprosthesis 100 from migrating after it has been implanted.

In alternative embodiments, the support structure 102 can comprise other shape memory alloys, or other materials capable of providing sufficient support for the bioprosthesis 100. Such materials can include other metals, metal alloys such as stainless steel or cobalt chromium, and/or polymers. The support structure 102 can have configurations other than that shown in FIG. 2. For example, the support structure 102 can have a different shape, more or fewer vertical support bars, and/or additional structures for added stability. The support structure 102 can comprise a strut mesh and/or sleeve structure.

The flexible membrane 104 is a valve member that is positionable in the flow path of the support structure 102 and that is configured to permit flow in a first direction but substantially resist flow in a second direction. In certain implementations, the flexible membrane 104 comprises a biological tissue formed into a valve member. The biological tissue which forms the valve member can comprise pericardial tissue harvested from an animal heart, such as porcine, bovine, or equine pericardium. The flexible membrane 104 can also comprise, alternatively or additionally, biocompatible materials including synthetic polymers such as polyglycolic acid, polylactic acid, and polycaprolactone, and/or other materials such as collagen, gelatin, chitin, chitosan, and combinations thereof.

The membrane support 106 can be positionable in the flow path and affixed to the support structure 102. Membrane support 106 can comprise polyethylene terephthalate (PET) (e.g., Dacron), or any other suitable material. The membrane support 106 can be positioned such that it folds under and around the bottom of the flexible membrane 104. The membrane support 106 can be sutured or otherwise affixed to the flexible membrane 104. In some embodiments, the membrane support 106 can comprise a skirt on the exterior surface of the flexible membrane 104, and a thinner ribbon on the interior surface of the flexible membrane 104, within the flow path. In this embodiment, the ribbon and skirt structures of the membrane support 106 can be sutured together, with a portion of the flexible membrane between them. In some embodiments, the membrane support 106 can be a thin layer of material, such as a layer of PET that can be from about 0.01 mm thick to about 0.2 mm thick. In some embodiments, the thickness of the membrane support 106 can vary from the center to the edge. For example, in one embodiment, the membrane support 106 can be about 0.07 mm thick at an edge, and about 0.05 mm thick at the center. In another specific embodiment, the membrane support 106 can be about 0.13 mm thick at the edge, and about 0.10 mm thick at the center. Additional details of the support structure 102, the flexible membrane 104, and the membrane support 106 are described in U.S. Pat. Nos. 6,730,188 and 6,893,460, both of which are hereby incorporated herein by reference. Furthermore, U.S. Pat. Nos. 6,730,188 and 6,893,460 describe additional prosthetic valve that can be modified according to the disclosed technology and used as part of any of the disclosed apparatus or systems or used with any of the disclosed methods or procedures.

In certain embodiments, grabbing mechanisms 108 are configured as strips of projections or micro-anchors 110. The grabbing mechanisms 108 can vary from implementation to implementation, but in certain implementations comprise any structure capable of at least partially penetrating and engaging the target tissue. For example, the projections 110 can be designed to at least partially penetrate and/or otherwise engage (e.g. by clamping or grabbing) the surrounding tissue upon over-expansion and to contract the aortic annulus and surrounding native tissue along with the support structure 102 upon recoil of the support structure 102. In other embodiments, the projections 110 may include barbed projections, umbrella projections, and/or hooks also designed to at least partially penetrate the tissue upon over-expansion and contract the aortic annulus and surrounding tissue upon recoil of the support structure 102.

As shown in FIG. 2, the grabbing mechanisms 108 can be positioned and coupled to the support structure 102 as vertical, or axial, strips of projections 110. In an alternative embodiment shown in FIG. 3, the grabbing mechanisms 109 can be positioned and coupled to the support structure 102 as one or more horizontal, or circumferential, strips of projections 111. For example, one or more strips of projections 111 can be disposed around the circumference of the support structure 102. Such grabbing mechanisms 109 can extend substantially around the circumference of the support structure 102, and/or strips of projections 111 can extend only partially around the circumference of the support structure 102, such as horizontal arcs of projections. In some embodiments, projections can be provided in one or more localized areas of the support structure 102, in addition to or instead of being provided in linear strips. In certain embodiments, one or more strips of projections can be provided along one or more struts or wires of the support structure 102, substantially paralleling the angles of the support structure 102. In another embodiment, the strips can be disposed circumferentially around the support structure 102 and located along the commissural supports (e.g. portions of the support structure wherein adjacent prosthetic leaflets meet and attach to the support structure) of support structure 102.

Some implementations of the bioprosthesis 100 shown in FIGS. 2 and 3 can comprise only one grabbing mechanism 108, 109. Alternative embodiments can comprise two or more grabbing mechanisms 108, 109. Further, the grabbing mechanisms 108, 109 can be manufactured separately from the support structure 102 and attached to the support structure through a suitable means (e.g., sutures, adhesive, weld, snap-fit mechanism, friction, and the like). Alternatively, the grabbing mechanisms 108, 109 can be formed as an integral feature of the support structure. Each grabbing mechanism 108, 109 generally comprises one or more projections or micro-anchors 110, 111. The projections or micro-anchors 110 can have any suitable dimension. For instance, the projections 110 can have a length from approximately 1 mm to approximately 2 mm Projections 110 can be smaller in some embodiments, such as having a length from about 0.001 mm to about 1 mm Alternatively, projections 110 can be larger in some embodiments, such as having a length from about 2 mm to about 6.5 mm or larger. In some embodiments, a grabbing mechanism 108, 109 can include a plurality of projections 110, where at least a first projection can be a different size from a second projection. A single grabbing mechanism can include a plurality of sizes of projections.

In some embodiments, the projections can be formed of a shape memory material that is configured to change shape. For instance, in one implementation, the projections can change shape after penetrating the tissue. For example, barbs at the tip of the projections can change in angle or configuration in relation to the projection after penetrating the tissue in order to more securely engage with the tissue. In another embodiment, the projections can change shape after expansion of the support structure 102. For example, the projections 110 can lay flat against the support structure 102 while the bioprosthesis is in its contracted configuration, and the projections can expand and the barbs can change shape to extend laterally outward from the projection to prevent the projection from slipping out of the tissue once the bioprosthesis 100 has been expanded.

In one variation, one or more projections can be configured with a delayed release mechanism, such that at least a portion of each projection changes shape after a period of time. This may be achieved by incorporating a resorbable material into the projection for temporarily holding the projection in a constrained condition. As the resorbable material is resorbed by the body, the projection becomes free to assume its relaxed condition. As the projection moves to its relaxed condition, its shape can change to more securely engage and hold the surrounding tissue. For example, barbs or hooks associated with the projection can initially be held against the main body portion of the projection until the resorbable material is resorbed. At that time, the barb or hook can extend outwardly from the main body portion, thereby creating a more secure attachment to the tissue in which the projection is inserted.

FIGS. 4-9 show elevation views of various embodiments of projections 400, 402, 404, 406, 408, 410 that can be used with embodiments of a transcatheter heart valve according to the present disclosure. In general, the projections 400, 402, 404, 406, 408 include a main body portion and one or more barbs. For instance, the illustrated projections include projection 400 with a single sharpened barb 401, projection 402 with a hook-shaped barb 403, projection 404 with an anchor-shaped (arrow head) barb 405, projection 406 with multiple branch-like barbs 407, projection 408 with multiple tree-shaped sharpened barbs 409, and hook-shaped projection 410. Suitable projections further include spikes, staples, fasteners, tissue connectors, or any other suitable projection capable of engaging with a patient's native tissue. Embodiments of suitable projections 400, 402, 404, 406, 408, 410 can be designed to penetrate the aortic valve annulus and engage or lodge within the thickness of the aortic valve annulus such that when the bioprosthesis retracts toward its natural state, the projections pull the patient's native tissue inward towards the center of the flow path, substantially without dislodging from their engaged positions. The barbs can be formed on the projections 400, 402, 404, 406 408 by laser cutting or other appropriate manufacturing method. Suitable materials for projections include Nitinol, other shape memory alloys, stainless steel, cobalt chromium, titanium, Elgiloy, HDPE, nylon, PTFE, other biocompatible polymers, resorbable materials, and combinations thereof. Other suitable materials are known in the art, and the projections of the present disclosure are not limited to those discussed.

Figure 21:
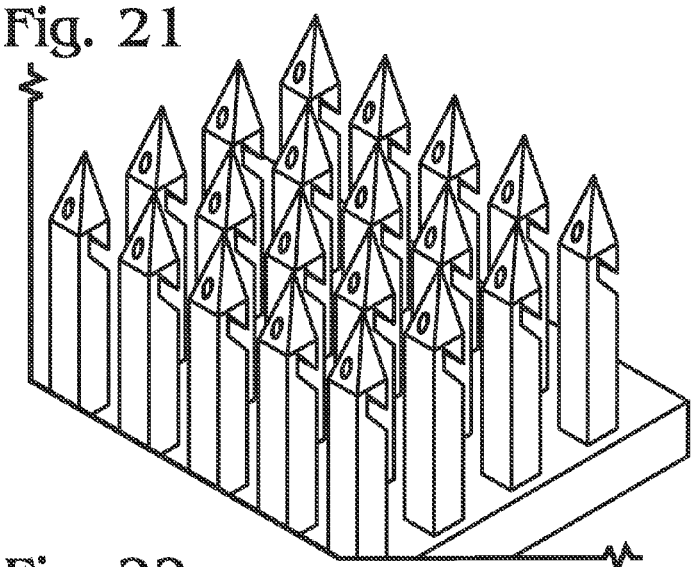
Figure 22:
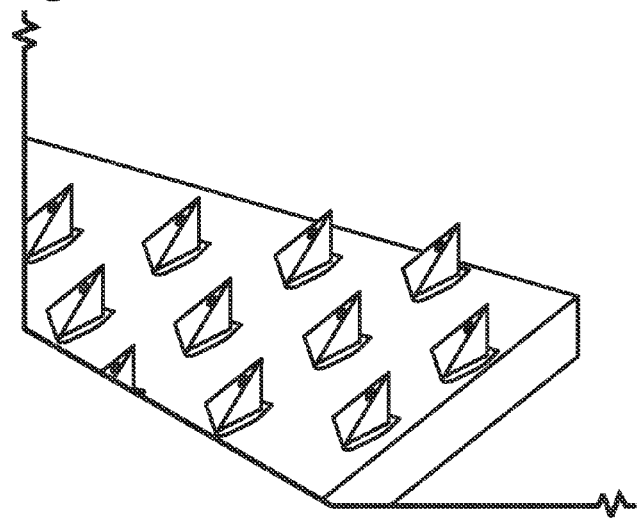
Figure 23:
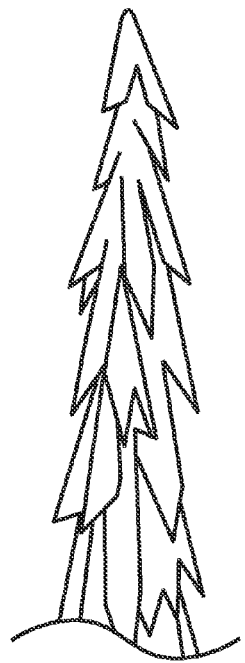

FIGS. 21-25 illustrate additional possible embodiments of projections 416, 418, 420, 422, 424. FIG. 21 shows a projection 416 that has a square cross-sectional base and a pyramidal pointed tip, wherein a cutout between the base and the tip can facilitate engagement within a patent's native tissue. FIG. 22 shows a pointed projection 418 that can extend at an angle from the surface of a support structure or bioprosthesis. FIG. 23 shows an asparagus tip-like projection 420. FIG. 24 shows a conical projection 422. FIG. 25 shows another embodiment of a tree-like projection 424.

FIG. 10 is a perspective view of another embodiment of a transcatheter heart valve 100a (also referred to as bioprosthesis 100a) according to the disclosed technology. Bioprosthesis 100a includes a support structure 102a having a tubular or cylindrical base, a flexible membrane 104a (e.g., valve member), a membrane support 106a and at least one grabbing mechanism 108a affixed about a circumference of the support structure 102a. The support structure 102a is expandable from a first reduced diameter to a second enlarged diameter, and has a flow path along a structural axis. The support structure 102a generally can include a tubular framework, such as a stent, which primarily secures bioprosthesis 100a within or adjacent to the defective valve annulus of the heart. In this embodiment, the support structure 102a is configured to approximate the shape of the flexible membrane 104a such that the upper end of support structure 102a comprises peaks at the commissure supports and valleys (e.g. U-shaped cusps) between the commissure supports.

FIG. 26 is a perspective view of another embodiment of a transcatheter heart valve having two attachable sections 700, 702 that can be delivered separately. This embodiment can reduce the cross-sectional profile during delivery because each section 700, 702 can have a smaller delivery profile than the entire assembled bioprosthesis. In the illustrated embodiment, outer section 700 comprises an outer stent structure 710, and inner section 702 comprises an inner stent structure 720 and a valve member 722. In this embodiment, the inner stent structure 720 and the valve member 722 together form the expandable prosthetic heart valve. The outer section 700 can optionally include a temporary valve member 712, which can be thinner or less durable than the more permanent valve member 722. The temporary valve member 712 can be mounted on or otherwise secured to the outer stent structure 710 using any suitable mechanism (e.g., sutures, snaps, screws, friction, hooks, barbs, adhesives, and/or a slide structure). Furthermore, the temporary valve member 712 can be configured to have a diameter and flexibility suitable to receive the inner section 702 during valve delivery. The valve member 722 can be any valve as described herein and can be mounted to or otherwise secured to the inner stent structure 720 using any suitable means (e.g., sutures, snaps, screws, a slide structure, friction, hooks, barbs, and/or an adhesive).

In some embodiments, the outer section 700 can comprise a thin compressible member 712 that can facilitate securing the inner section 702 within the outer section 700. Such a compressible member 712 can create a tight seal between the outer section 700 and the inner section 702 as the inner section presses into the compressible material. Further details regarding a compressible member 712 are disclosed in U.S. Patent Application Publication No. 2008/0208327, which is hereby incorporated herein by reference.

According to one exemplary delivery procedure, and as more fully explained below in connection with FIGS. 16-20, the outer section 700 is delivered to the aortic valve first. The outer stent structure 710, like embodiments discussed above, can comprise a shape memory alloy such as Nitinol, and can have a predetermined recoil (or natural) diameter. The outer section 700 can be over-expanded to a diameter greater than its recoil diameter. For example, the outer section 700 can be disposed around a balloon catheter and delivered to the interior of the native heart valve. The balloon of the balloon catheter can then be inflated, causing the outer section 700 to expand to a diameter beyond its recoil diameter. In particular implementations, the outer section 700 comprises one or more grabbing mechanisms 708 configured to engage with the native tissue when the outer stent structure 710 is over-expanded. For example, the grabbing mechanisms 708 can be any of the grabbing mechanisms described above. Once the balloon of the balloon catheter is deflated and removed, the outer section 700 will contract to its memorized or recoil diameter. On account of the engagement of the grabbing mechanisms 708 to the surrounding tissue, the contraction of the outer section 700 will cause the size of the aortic annulus to be reduced as well. Inner section 702 can then be delivered and engaged with the outer section 700.

In an alternative method of delivering the two part bioprosthesis, the outer section 700 can be delivered to the interior of a native heart valve in a crimped state, and allowed to expand to its predetermined natural diameter, once positioned. A balloon can then be inserted within the outer section 700. When the balloon is expanded, the outer section can be over-expanded to a diameter greater than its natural diameter to allow the grabbing mechanisms of the outer section 700 to engage with the native valve tissue. When the balloon is deflated, contraction of the outer section 700 can cause the size of the aortic annulus to be reduced. When compared to the previous method, this can allow for delivering the outer section 700 in a smaller crimped state, because the outer section 700 is not crimped over the balloon for delivery; the balloon is not inserted until after the outer section 700 is first allowed to expand to its natural diameter. Inner section 702 can then be delivered and engaged with the outer section 700.

Figure 11:
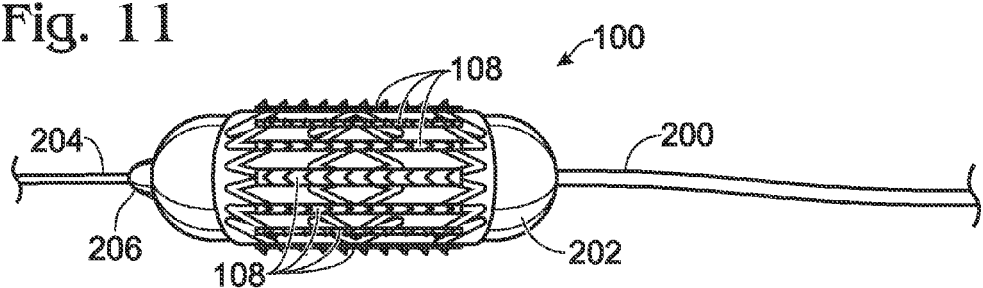
FIG. 11 is a simplified side view of a balloon catheter delivery system that is configured to over-expand the shape memory support structure at a target area inside a patient's body in accordance with an embodiment of the disclosed technology.

FIG. 11 is a simplified illustration of a balloon catheter 200, which can be used to deliver and deploy a bioprosthesis (such as bioprosthesis 100 shown in FIG. 2 above) into a native heart valve. In one embodiment, the balloon catheter 200 advances the bioprosthesis 100 through an outer sheath of the delivery system over a guide wire 204. The balloon catheter 200 can also be configured to aid in the delivery and positioning of the bioprosthesis 100 within the native valve. For example, as shown in FIG. 11, the balloon catheter 200 can include a tapered nose cone tip 206 at its distal end that allows a balloon portion 202 and bioprosthesis 100 to cross easily into the native valve. The balloon portion 202 can be inflated (e.g., using a controlled volume of saline), causing the bioprosthesis 100 to expand within and engage the native hart valve.

In one exemplary method, the guide wire 204 is inserted into the femoral artery of a patient, advanced through the aortic arch of a patient, and into the aortic valve. The balloon catheter 202 is advanced through the outer sheath of the delivery system, over the guide wire 204, and into the aortic valve. The bioprosthesis 100 is then positioned and secured within the native valve by inflating the balloon portion 202. FIGS. 12-15, described below, illustrate one exemplary procedure for deploying the bioprosthesis 100 into the native valve. The balloon portion 202 can then be deflated, and the balloon catheter 202 retracted from the patient's aorta and femoral artery. An exemplary delivery system designed to deliver the bioprosthesis 100 is the RETROFLEX II catheter assembly available from Edwards Lifesciences in Irvine, Calif. Furthermore, although the operation described above is a percutaneous transfemoral procedure, it should be understood that embodiments of the disclosed technology include the use of a shorter catheter assembly or semi-rigid cannula for deploying a bioprosthesis in a minimally invasive surgical (MIS) procedure, such as a trans-apical procedure. In a transapical procedure, the catheter or cannula is inserted through a gap between the ribs and is advanced through a small incision formed along the apex of the heart. This technique advantageously provides the surgeon with a direct line of access to the aortic valve. U.S. Patent Application Publication Nos. 2008/0065011, 2007/0005131, and 2007/008843 disclose further details regarding suitable delivery methods, and are hereby incorporated herein by reference.

Figure 12:
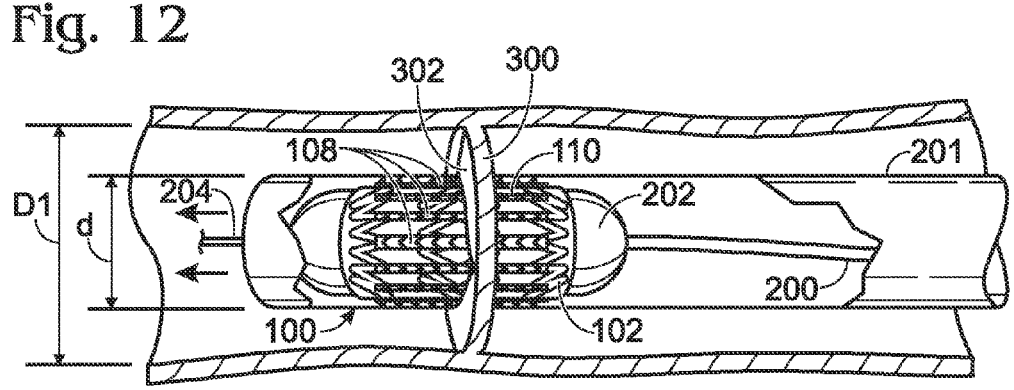

FIGS. 12-15 are schematic cross-sectional views of a patient's aorta illustrating delivery of the support structure and valve of FIG. 2. As shown in FIG. 12, in one embodiment, the bioprosthesis 100 may be introduced into the patient's body using a percutaneous delivery technique with the balloon portion 202 of the balloon catheter 200 deflated, and the bioprosthesis 100 operably disposed thereon. The bioprosthesis can be contained in a radially crimped or compressed state. In embodiments using a self-expandable bioprosthesis 100, the bioprosthesis 100 can be held in a compressed state for delivery, by, for example, containing the bioprosthesis within an outer covering or sheath 201. The outer covering 201 can be removed or retracted, or the bioprosthesis 100 pushed through the outer covering 201, to allow the self-expandable bioprosthesis 100 to self-expand. In embodiments having a bioprosthesis that does not self-expand, such an outer covering may not be needed to retain the bioprosthesis in a crimped state, but can nonetheless be used if desired (e.g. to reduce friction during delivery).

In the embodiment illustrated in FIG. 12, the projections 110 of the grabbing mechanisms 108 are disposed around the outside circumference of support structure 102.

In the illustrated embodiment, the bioprosthesis 100 is introduced and positioned across the native aortic valve annulus (AVA) 300 by being inserted at least partially through native valve leaflets 302 and expanded. Because the AVA of an aortic valve suffering from aortic insufficiency is dilated, diameter D1 of the AVA 300 is expected to be larger than the diameter of a healthy AVA.

Figure 13:
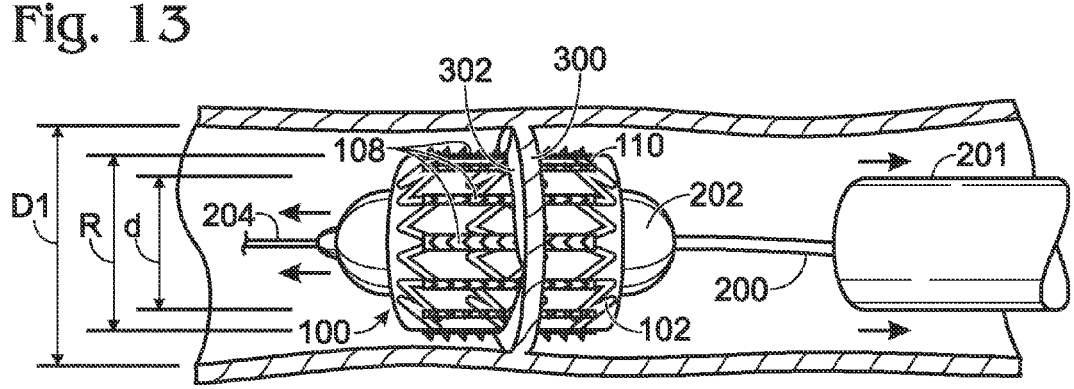

As shown in FIG. 13, outer sheath or covering 201 can be retracted or removed from over the bioprosthesis 100. In embodiments having a bioprosthesis 100 comprising a shape memory alloy, the bioprosthesis can expand from its crimped or compressed diameter d to a predetermined or memorized diameter R once the sheath 201 is removed.

As shown in FIG. 14, the balloon portion 202 of the balloon catheter 200 is expanded to increase the diameter of the support structure 102 from its relaxed diameter R (FIG. 13) to an over-expanded diameter OE such that the outer diameter of the bioprosthesis 100 equals or exceeds the original diameter D1 of the AVA 300. In this manner, the AVA 300 may expand beyond the diameter D1 as well. During the expansion, the projections 110 of the grabbing mechanisms 108 are forced to contact and can penetrate or otherwise engage (e.g. clamp or grab) the target tissue, which may include the AVA 300 and some of the tissue surrounding the AVA. This causes the bioprosthesis 100 to adhere to the surrounding tissue.

Next, as shown in FIG. 15, the balloon portion 202 of the balloon catheter 200 can be deflated, and the balloon catheter 200 removed from the AVA 300. In embodiments where the support structure 102 is formed of a shape memory material, removing the expansion force of balloon 202 from support structure 102 allows the support structure 102 to return from an over-expanded diameter OE (FIG. 14) to a recoil or relaxed diameter R. The manufacture of the support structure (i.e., stent) determines what the recoil diameter will be. For example, the recoil diameter of a support structure comprising a shape memory alloy can be the memorized or functional diameter of the support structure. The recoil diameter of a support structure comprising, for example, stainless steel and/or cobalt chromium can be that of the natural or resting diameter of the support structure, once it inherently recoils from being over-expanded by the balloon 202. As the diameter of bioprosthesis 100 decreases to the recoil diameter R, the diameter of the AVA 300 also decreases to a final diameter D2. The AVA 300 can decrease in diameter due to the projections 110 of the support structure 102 pulling the target tissue inward.

An existing bioprosthesis is generally configured to be radially expanded to a diameter capable of providing secure fixation in a dilated AVA. However, as discussed above, existing bioprostheses are not well suited for treating aortic insufficiency due to the lack of firm tissue in the aortic annulus. Using existing technology, a larger bioprosthesis could be used to create a more secure fixation; however, a larger bioprosthesis cannot be easily crimped down for delivery via a catheterization technique. In contrast, embodiments of the present bioprosthesis 100 allow for the collapsed diameter of bioprosthesis 100 to be a smaller diameter because bioprosthesis 100 may be assembled with a smaller stent and a smaller valve member. This smaller size is possible because, rather than stretch the AVA, the present bioprosthesis advantageously reduces the diameter of the AVA during implantation. As a result, a smaller overall structure can be achieved which allows the support structure 102 of bioprosthesis 100 to be crimped to the smaller collapsed diameter and thus have a smaller profile for delivery through a patient's vasculature. For example, in some embodiments, bioprosthesis 100 can be crimped to a size of from about 4 French to about 7 French.

In alternative embodiments, the bioprosthesis 100 need not be operably disposed on the balloon 202 during delivery. For example, the bioprosthesis 100 can be crimped onto the catheter 200 at a different location than the balloon 202. The bioprosthesis can be allowed to self-expand once positioned within a patient's native aortic valve, and the balloon 202 can be positioned inside the self-expanded bioprosthesis 100 and inflated to then over-expand the bioprosthesis 100.

Figure 17:
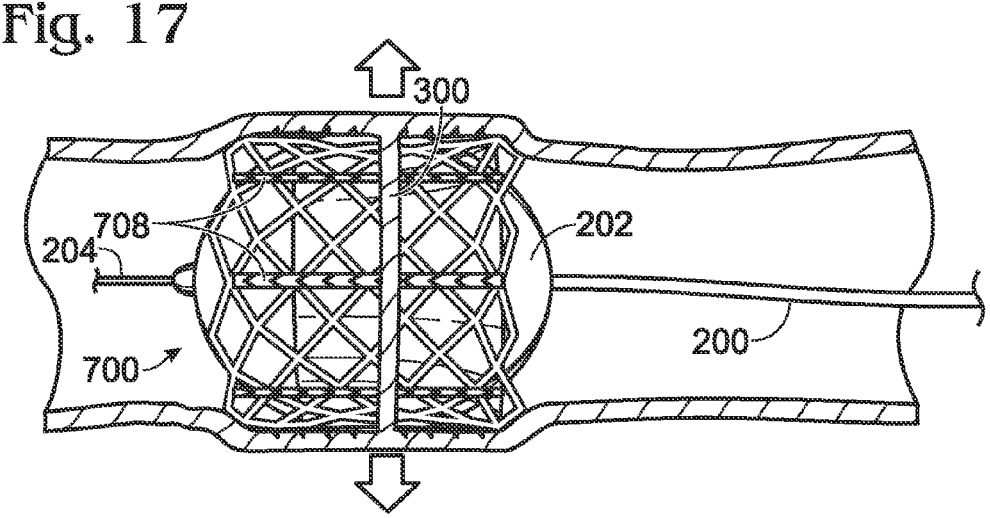

FIGS. 16-20 show simplified elevation views of one embodiment of a transcatheter heart valve being deployed in a two-stage process according to one method of the present disclosure. The illustrated method can be used, for example, to deliver the transcatheter heart valve assembly shown in FIG. 11. In the method illustrated in FIGS. 16-20, the outer section 700 can be deployed to the aortic valve separately from valve member 702. FIG. 16 shows the outer section 700 on a balloon 202, positioned inside the leaflets 302 of the aortic valve annulus 300. The outer section 700 can be a self-expanding stent, such as a stent comprising a shape memory alloy, or the outer section 700 can be simply balloon expandable, such as a stent comprising stainless steel, cobalt chromium and/or other suitable biocompatible materials. FIG. 17 shows the balloon 202 in an inflated configuration, which can expand the outer section 700 such that grabbing mechanisms 708 engage with the native tissue of the leaflets 302 and/or the aortic valve annulus 300.

Figure 18:
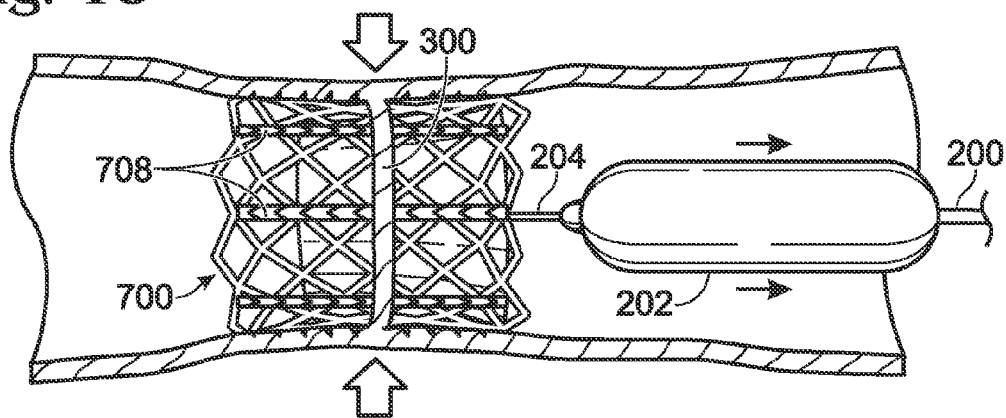
Figure 19:
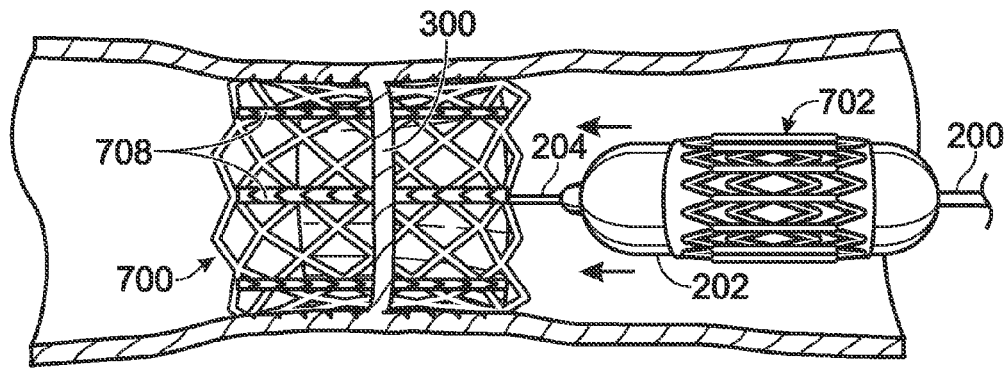
Figure 20:
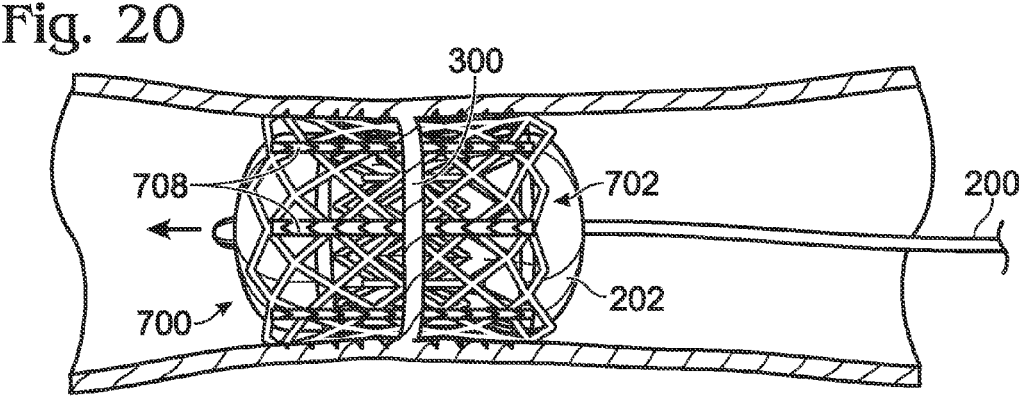

As shown in FIG. 18, the balloon 202 can be deflated and removed. The outer section 700 can reduce the diameter of the aortic valve annulus 300 as it retracts after the balloon 202 is removed. The outer section 700 can retract to a functional or memorized diameter if it comprises a shape memory alloy, or the outer section 700 can simply naturally recoil or retract due to the ductility of the material. The inner section 702 can be positioned within the outer section 700 using a catheter 200 and a balloon 202, as shown in FIG. 19. As shown in FIG. 20, the balloon 202 can be expanded, thus expanding the crimped inner section 702, allowing it to engage with the outer section 700.

The outer section 700 and the inner section 702 can be delivered on a single catheter 200 or on separate catheters. For example, a catheter 200 can include two expandable balloons, one distal to the other. A first balloon can be used to expand the outer section 700 then deflated and either guided through the lumen of the expanded outer section 700 or removed back through the lumen. The second balloon and inner section 702 can then be positioned within the outer section 700, and the second balloon can be expanded, allowing for the inner section 702 to engage with the outer section 700. The second balloon can then be deflated, and the catheter 200 removed, thus removing the first and second balloons. In alternative embodiments, separate catheters can be used, such that a first catheter is used to deliver a first balloon and the outer section 700 to the native valve, and a second catheter is used to deliver a second balloon and the inner section 702 to the native valve once the outer section has been deployed and the first catheter has been removed.

While FIG. 16 illustrates the outer section 700 being delivered while already crimped on the balloon 202, in alternative embodiments, the outer section 700 can be located at a different position on the catheter 200 than the balloon 202. For example, in some embodiments, a crimped outer section 700 can be delivered to a native aortic valve and allowed to self-expand, such as by removing an outer covering. The balloon 202 can then be positioned within the expanded outer section 700 and inflated, thereby over-expanding the outer section 700, allowing the grabbing mechanisms 708 to engage with the native tissue. The balloon can then be deflated and removed, and the inner section 702 can be delivered and engaged with the outer section 700.

It should be understood that embodiments of bioprosthesis 100 can be deployed using a non-inflatable, mechanical embodiment of delivery catheter 200. Furthermore, bioprosthesis 100 can be delivered using any suitable delivery method, including both transapical and femoral artery delivery methods. Additionally, although the disclosed embodiments concern aortic valve replacement, embodiments of the disclosed technology can be used to replace any dilated heart valve (e.g., a dilated mitral valve). Moreover, although bioprosthesis 100 is used as an exemplary embodiment of the disclosed technology, it should be understood that bioprosthesis 100 and bioprosthesis 100a may be considered interchangeable with one other, or with any other bioprosthesis made or adapted in accordance with the teachings of the disclosed technology.

Having illustrated and described the principles of the disclosed technology, it will be apparent to those skilled in the art that the disclosed embodiments can be modified in arrangement and detail without departing from such principles. In view of the many possible embodiments to which the principles of the disclosed technologies can be applied, it should be recognized that the illustrated embodiments are only preferred examples of the technologies and should not be taken as limiting the scope of the invention. Rather, the scope of the invention is defined by the following claims and their equivalents. I therefore claim all that comes within the scope and spirit of these claims.

I claim:

1. A system for treating aortic insufficiency, comprising:
   a delivery catheter comprising an elongate body and a balloon disposed along a distal end portion of the elongate body;
   a self-expandable support structure configured to be radially compressible into a compressed state for advancement through a patient's body via the delivery catheter, the support structure having a preset diameter to which the support structure recoils following expansion to an over-expanded diameter larger than the preset diameter;
   a flexible valve member secured within an interior of the support structure; and
   a plurality of grabbing mechanisms disposed along an outer surface of the support structure, the grabbing mechanisms configured to penetrate native tissue of an aortic valve for reducing a diameter of the aortic valve by pulling the native tissue of the aortic valve inwards when the support structure recoils from the over-expanded diameter to the preset diameter without dislodging from their engaged positions.

2. The system of claim 1, wherein the grabbing mechanisms comprise a projection having a hook, a sharpened barb, tree-shaped barbs, or an anchor-shaped barb.

3. The system of claim 1, wherein the grabbing mechanisms are formed of a shape memory alloy.

4. The system of claim 1, wherein the flexible valve member is a valve assembly formed of pericardial tissue.

5. The system of claim 4, wherein the valve assembly comprises three leaflets configured to replace the function of the aortic valve.

6. The system of claim 1, wherein the grabbing mechanisms comprise a strip of projections disposed circumferentially around the support structure.

7. The prosthetic heart valve of claim 1, wherein the grabbing mechanisms comprise a strip of projections disposed along a vertical axis of the support structure.

8. The prosthetic heart valve of claim 1, wherein the grabbing mechanisms include a projection that changes shape after a period of time.

9. The prosthetic heart valve of claim 8, wherein the projection is initially held in an undeployed state by a resorbable material.

10. A system for treating aortic insufficiency, comprising:
a self-expandable outer support structure configured to be radially compressible for delivery via a catheterization technique, the support structure having a first diameter to which the support structure recoils following expansion to a second diameter greater than the first diameter;
a plurality of grabbing mechanisms disposed on an outer surface of the outer support structure, the grabbing mechanisms configured to penetrate native tissue of the aortic valve and to reduce a diameter of the aortic valve by pulling the native tissue of the aortic valve inwards when the support structure recoils from the second diameter to the first diameter without dislodging from their engaged positions;
an inner support structure configured to be radially compressible and expandable into an expanded state within the interior of the outer support structure; and
a flexible valve member secured within an interior of the inner support structure.

11. The system of claim 10, wherein the grabbing mechanisms comprise a projection having a hook, a sharpened barb, tree-shaped barbs, or an anchor-shaped barb.

12. The system of claim 10, wherein any one or more of the outer support structure, the inner support structure, or the grabbing mechanisms are formed of a shape memory alloy.

13. The system of claim 10, wherein the flexible membrane is formed of pericardial tissue.

14. The system of claim 10, wherein the inner support structure is configured to self-expand into engagement with the outer support structure.

* * * * *